United States Patent [19]
Seki et al.

[11] Patent Number: 5,138,264
[45] Date of Patent: Aug. 11, 1992

[54] APPARATUS FOR MEASURING ELECTRICAL CONDUCTIVITY

[75] Inventors: Kiwao Seki; Koji Tsutsuta, both of Katsuta, Japan

[73] Assignee: Hitachi, Ltd., Tokyo, Japan

[21] Appl. No.: 456,454

[22] Filed: Dec. 26, 1989

[30] Foreign Application Priority Data

Dec. 29, 1988 [JP] Japan .................. 63-331790

[51] Int. Cl.⁵ .................. G01N 27/08; G01R 27/22
[52] U.S. Cl. .................. 324/439; 324/444; 324/709; 324/713; 324/720
[58] Field of Search ............... 324/439, 443, 444, 709, 324/713, 720

[56] References Cited

U.S. PATENT DOCUMENTS

| | | | |
|---|---|---|---|
| 3,778,707 | 12/1973 | Vogel | 324/709 X |
| 3,868,315 | 2/1975 | Forster et al. | 208/6 |
| 4,513,248 | 4/1985 | Miller | 324/439 |
| 4,969,363 | 11/1990 | Mochizuki | 324/439 X |
| 5,008,627 | 4/1991 | Tsutsuta et al. | 324/444 |

FOREIGN PATENT DOCUMENTS 53-003872 1/1978 Japan .
61-178457 11/1986 Japan .
62-167456 7/1987 Japan .

Primary Examiner—Kenneth A. Wieder
Assistant Examiner—Glenn W. Brown
Attorney, Agent, or Firm—Fay, Sharpe, Beall, Fagan, Minnich & McKee

[57] ABSTRACT

An electrical conductivity measuring apparatus for measuring the electrical conductivity of liquid has a plurality of electrodes disposed in the liquid contained in a measuring cell, with an a.c. voltage being applied between the electrodes, thereby measuring the electrical conductivity by measuring a current flowing between the electrodes. The apparatus includes a reference a.c. voltage source including adjustment means for varying the magnitude and phase of the signal current, and is designed to cancel the conductivity of background by adding the current from the reference a.c. voltage source to the current from the electrodes.

12 Claims, 9 Drawing Sheets

RL: LOAD RESISTANCE

APPARATUS FOR MEASURING ELECTRICAL CONDUCTIVITY

BACKGROUND OF THE INVENTION

This invention relates to an apparatus for measuring the electrical conductivity of liquid, and particularly to an electrical conductivity measuring apparatus having a phase compensation circuit and suitable for the equipment based on a.c. voltage application.

Conventionally, a small change in the electrical conductivity of an electrolyte having a large electrical conductivity is measured by applying, to the background compensation resistor, a voltage equal in magnitude and opposite in polarity to the voltage applied to the measuring cell which contains the electrolyte, and by summing the output current from the resistor and the output current from the measuring cell.

This method is used mainly for measuring the electrical conductivity of a sample by detecting the variation of electrical conductivity of the solvent (electrolyte) before and after the sample is resolved in it.

In the above-mentioned conventional technique, the resistance of the resistor is adjusted before the occurrence of a small variation of electrical conductivity so as to nullify the output of the adder, so the varying component of the adder output is proportional to the varying component of electrical conductivity.

Techniques similar to the above-mentioned prior art are disclosed in JP-A-61-178457(U) and JP-A-62-167456, for example.

A method of measuring the electrical conductivity of solution based on d.c. voltage application is disclosed in JP-A-53-3872. This method is a 4-electrode method based on d.c. voltage application, and is said to be free from the variation attributable to the surface conditions of the electrodes and the influence of polarization phenomenon, allowing high accuracy measurement. The method is completely different in both principle and structure from the measuring method of the present invention.

A U.S. patent application Ser. No. 07/420,479 filed on Oct. 12, 1989 discloses an electrical conductivity measuring apparatus in which the above-mentioned resistor is adjusted automatically.

SUMMARY OF THE INVENTION

The conventional technique used with an electrical conductivity measuring apparatus based on a.c. voltage application described above unfavorably lacks the taking into consideration of the electrostatic capacity created around the measuring cell due to the polarization action, and therefore the measuring cell must be dealt with as a composite circuit of resistors and capacitors, instead of pure resistors. Consequently, there arises a phase difference between the application voltage and the current of the measuring cell, creating also a phase difference between the current flowing in the background compensation resistor and the current flowing in the measuring cell, and the output of the compensation circuit cannot be brought to zero through the adjustment of the background compensation resistor.

It is possible to nullify apparently the output of the compensation circuit by use of a rectifying means which rectifies the compensation circuit output in synchronism with the a.c. voltage applied to the measuring cell. The balance point obtained here differs from the case of zero amplitude resulting from the subtraction of an in-phase sinusoidal wave. That is, the balance point here is obtained when the d.c. component of a sinusoidal wave, which is out of phase by $$\frac{\pi}{2} (90°)$$

with the synchronous rectification, falls to zero, the sinusoidal wave being formed by adding a sinusoidal wave of different phase to the cell current. Accordingly, a large a.c. signal remains and if the signal amplifier is set to have an increased gain for the high sensitivity analysis, the operational circuit of conductivity will have a problem of saturation. Moreover, in the conventional technique, in which a large signal is subjected to synchronous rectification, the variation of phase of this large signal develops a noise, and a high S/N ratio cannot be accomplished.

An object of this invention is to provide an electrical conductivity measuring apparatus capable of removing the background completely and performing the measurement of electrical conductivity of various electrolytes.

Another object of this invention is to provide an electrical conductivity measuring apparatus, the conductivity operational circuit of which is not saturated even if the cell signal amplifying circuit has a high gain, and therefore is suitable for use in the high sensitivity analysis, allowing the measurement of a small change of electrical conductivity of electrolyte having a large electrical conductivity.

A further object of this invention is to provide an electrical conductivity measuring apparatus which offers a high S/N ratio.

According to one aspect of this invention, in order to achieve the above objectives, the electrical conductivity measuring apparatus comprises a first generation means which is connected to a cell that contains electrolyte and generates a prescribed constant a.c. voltage to be applied to the cell; a synchronous rectifying means which is connected to the cell and rectifies an a.c. signal flowing through the cell; a second generation means which generates a compensation current for cancelling a background current, that flows through the cell, on the basis of the a.c. voltage, the compensation current being out of phase by $\pi$ (180°) with the a.c. voltage; and a summing means which is connected between the cell and rectifying means and sums the background current and compensation current so as to cancel the background current; wherein the second generation means is provided with a means of correcting the phase of the compensation current in response to the phase deviation of the background current from the a.c. voltage.

According to a preferred embodiment of this invention, the phase correction for the compensation current is based on the principle of vectorial summation. Namely signals with the same frequency are summed, with the magnitude and phase of the addend signal being varied, and an arbitrary phase can be produced.

A compensation current equal in magnitude and out of phase by $\pi$ (180°) with the a.c. current flowing through the measuring cell due to the application of the a.c. voltage is produced and it is added to the current from the cell, and the background current can be nullified in both d.c. and a.c. modes.

In the absence of the background current, the gain of the signal amplifier can be made higher, and a small cell current, i.e., a small change in the electrical conductivity in proportion to the cell current, can be measured. The signal after the background compensation or removal has no a.c. component, and a phase variation caused by synchronous rectification does not create a noise or drift.

The behavior of the inventive apparatus will be detailed. The prescribed a.c. voltage applied to the measuring cell is expressed as follows.

$$V_C(\omega) = V_C \sin \omega t$$

where $V_C$ is the peak value of the cell application voltage, $\omega$ is the angular velocity of the cell application voltage, and t is the time.

The current flowing through the cell is expressed as follows.

$$I_{CE}(\omega) = K \sigma V_C \sin(\omega t + \theta)$$

where K is a constant of proportion, $\sigma$ is the electrical conductivity, and $\theta$ is a phase shift created by the electrostatic capacity of the cell.

When the electrical conductivity of the cell varies from $\sigma$ to $\sigma + \Delta\sigma$, the cell current becomes as follows.

$$I_{CE}(\omega) = K (\sigma + \Delta\sigma) \sin(\omega t + \theta)$$

Accordingly, the variation of cell current is proportional to the variation of electrical conductivity. For the high sensitivity measurement, the cell current needs to be amplified at a high gain. However, $\sigma$ is incomparably larger than $\Delta\sigma$ in general, and the amplifier cannot have a higher gain, since the operational circuit is saturated by the $\sigma$ component.

On this account, a conventional manner of background compensation is to produce a signal for removing the $\sigma$ component and subtract the signal from the cell current so that only the $\Delta\sigma$ component is left remaining. The $\sigma$ component removal signal is produced from the cell application voltage $V_C(\omega)$ using an inverting amplifier and resistors.

This method is based on the following equations for an electrical conductivity of $\sigma$.

$$I_0 = K\sigma V_C \sin(\omega t + \theta) - B \cdot V_C \sin \omega t$$
$$= C \sin(\omega t + \alpha)$$

$$C = \sqrt{(-B + K\sigma \cos\theta)^2 + K^2\sigma^2 \sin^2\theta} \cdot V_C$$

$$\alpha = \tan^{-1}\left(\frac{K\sigma \sin\theta}{-B + K\sigma \cos\theta}\right)$$

where $I_O$ is the output after compensation, and B is a proportional factor of the compensation current.

With the value of B being made variable and set to $B = K\sigma \cos\theta$, $\alpha$ becomes equal to $$\frac{\pi}{2},$$

and then, $$I_0 = V_C K\sigma \sin\theta \sin\left(\omega t + \frac{\pi}{2}\right)$$

This equation reveals that $I_O$ has its phase shifted by $$\frac{\pi}{2}$$

relative to the phase of synchronous rectification. Accordingly, by taking synchronous rectification, its d.c. component is nullified, and the background can be compensated. In this connection, the synchronous rectification at this time is based on $\sin \omega t$, and it alternates the rectification phase angles of $\omega t = n\sigma$ (n=0, 1, 2, ...).

However, an a.c. component having an amplitude of $V_C \cdot K\sigma \sin\theta$ still remains in the operational circuit. The value of $\theta$ is small in general and the amplitude can be made smaller as compared with the case before the compensation, although it imposes a problem with more sensitive measurement.

According to the present invention, a phase shift circuit is used to produce a signal to be added to $V_C(\omega)$ which signal differs in phase from $V_C(\omega)$ thereby to produce the compensation current Ico, as follows.

$$I_{CO} = a \cdot V_C \sin\omega t + b \cdot V_C \sin(\omega t + \beta)$$
$$= \sqrt{(a + b \cdot \cos\beta)^2 + b \cdot \sin\beta} \cdot V_C \cdot \sin(\omega t + \beta')$$

$$\beta' = \tan^{-1}\frac{b \cdot \sin\beta}{a + b\cos\beta}$$

By varying the value of a and b, an arbitrary signal can be produced. Here, the signal is designed to have the same amplitude and different phase with respect to the background cell current, as follows.

$$K\sigma = \sqrt{(a + b \cdot \cos\beta)^2 + b \cdot \sin\beta}$$

$$\theta + \pi = \beta' = \tan^{-1}\frac{b \cdot \sin\beta}{a + b\cos\beta}$$

By adding the compensation current to the cell current, both of the a.c. component and d.c. component can be nullified.

DESCRIPTION OF THE PREFERRED EMBODIMENTS

The present invention will be described with reference to the drawings.

Figure 1:
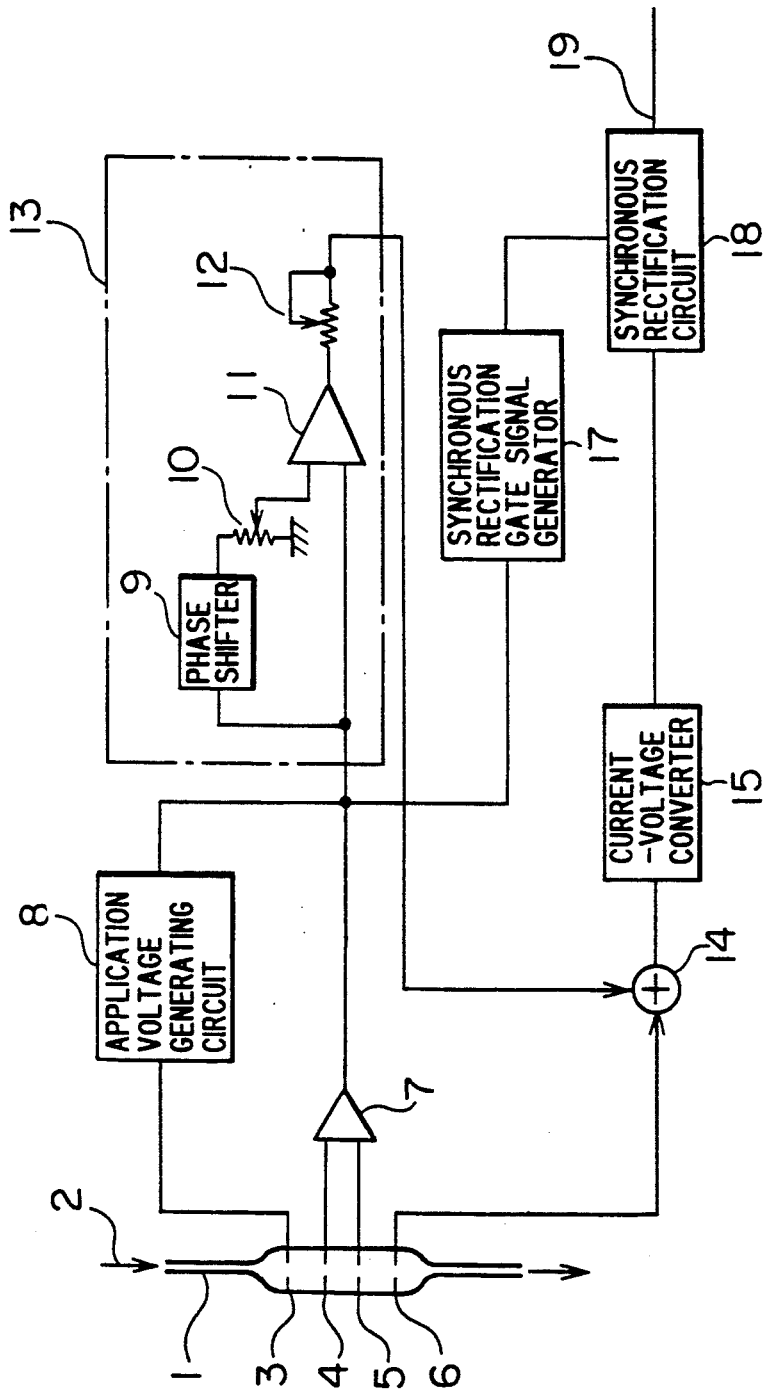
FIG. 1 is a block diagram showing an embodiment of the electrical conductivity measuring apparatus according to this invention.

FIG. 1 is a block diagram showing an embodiment of the inventive electrical conductivity measuring apparatus. In the figure, indicated by 1 is a measuring cell, 2 is electrolyte, 3 is a first electrode, 4 is a second electrode, 5 is a third electrode, 6 is a fourth electrode, 7 is a differential amplifier, and 8 is an application voltage generating circuit. A compensation current generation circuit 13 is made up of a phase shifter 9, a mixing ratio adjuster 10, an adder 11, and a background compensation value adjuster 12. The phase shifter 9, mixing ratio adjuster 10 and adder 11 constitute a phase correction circuit which corrects the phase of the compensation current.

Indicated by 14 is a current adder, 15 is a current-voltage converter, 17 is a synchronous rectification gate signal generation circuit, 18 is a synchronous rectification circuit which is known, and 19 is an output signal. The measuring cell 1 incorporates the electrodes 3–6 that are exposed to the flow of electrolyte 2. An a.c. voltage is applied to the first electrode 3 against the fourth electrode 6 which is at the ground voltage.

The output signal 19 is delivered through a filter and amplifier (not shown) to a calculation circuit (not shown), by which the electrical conductivity is calculated.

The application voltage generation circuit 8 is controlled by the output signal of the differential amplifier 7 so that the magnitude $V_{C23}$ of potential difference 5 of the cell 1 is constant. Accordingly, the differential amplifier 7 always produces an a.c. voltage of constant amplitude equivalent to the potential difference of the second and third electrodes 4, 5.

The current flowing out of the cell 1 is converted into a voltage by the current-voltage conversion circuit 15, and it is converted into a d.c. output 19 by the synchronous rectification circuit 18.

The following equations result.

$$I_C = \sigma_{23} \cdot V_{C23}$$
$$\sigma_{23} = I_C/V_{C23}$$

where $I_C$ is the cell current, $\sigma$ is the electrical conductivity between the second and third electrodes 4, 5, and $V_{C23}$ is the potential difference between the second and third electrodes.

Since $V_{C23}$ is constant, $\sigma$ is proportional to $I_C$, and the electrical conductivity of electrolyte 2 can be evaluated by measuring the current of the cell 1.

In the case of measuring a small change in the electrical conductivity at high sensitivity, the measuring circuit needs to have an increased gain. However, if the electrical conductivity of the background before a change occurs is large, the cell saturated when the gain is simply raised.

Figure 2:
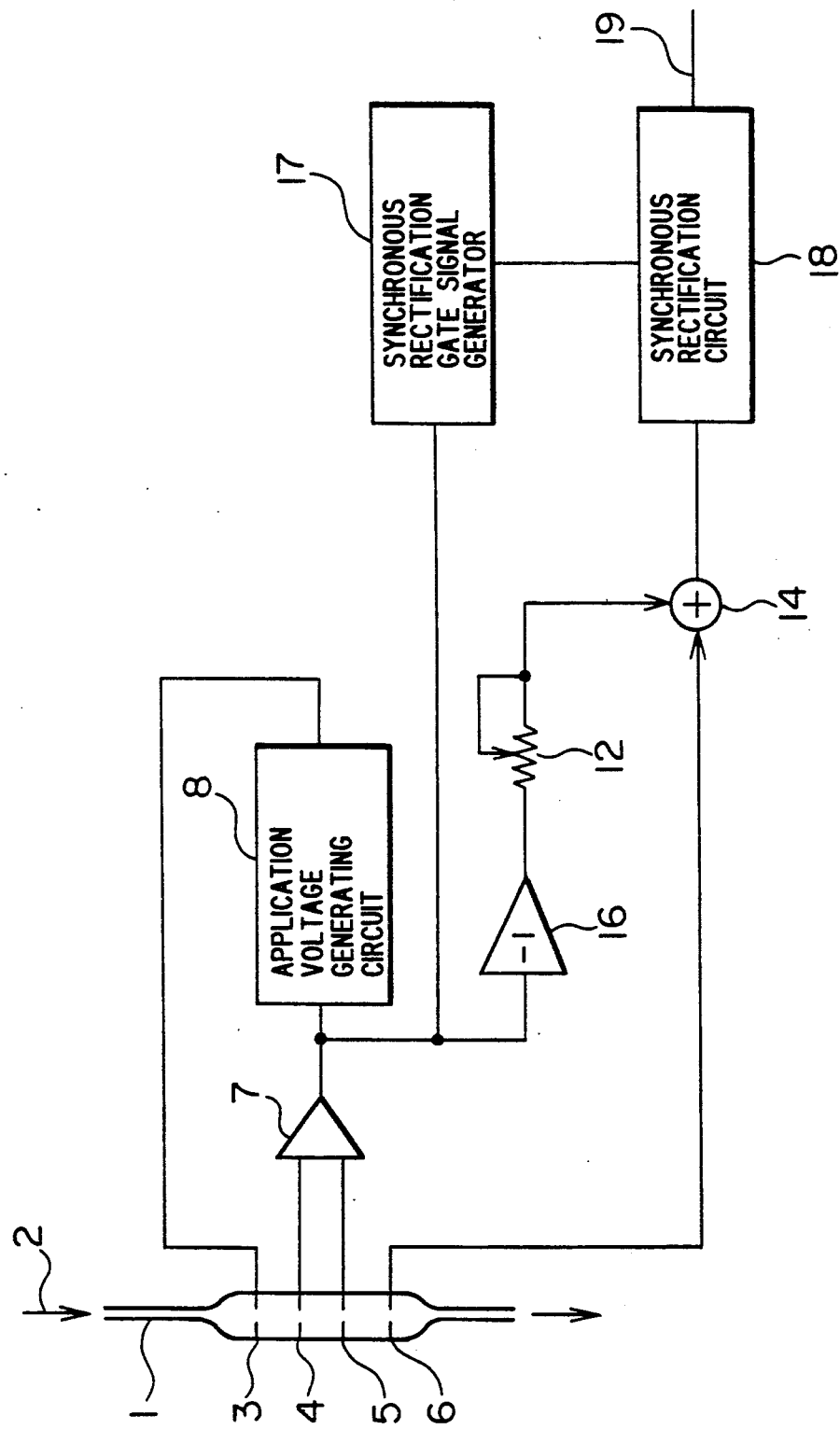
FIG. 2 is a block diagram showing the internal arrangement of the conventional electrical conductivity measuring apparatus.

Conventionally, as disclosed in the above-mentioned JP-A-61-178457(U) for example, a voltage which is equal in magnitude to the cell application voltage and having its polarity reversed by the inverting amplifier 16 is applied to the resistor 12, and the current from the resistor 12 is added to the cell current, as shown in FIG. 2. When the electrical conductivity of the resistor 12 becomes equal to that of the cell 1, the output of the current adder 14 goes zero and the successive circuit will not be saturated even if the gain is raised. This adjustment is named "background compensation". After the "background compensation", the current adder 14 has its output being proportional to the amount of change of the electrical conductivity.

Figure 3A:
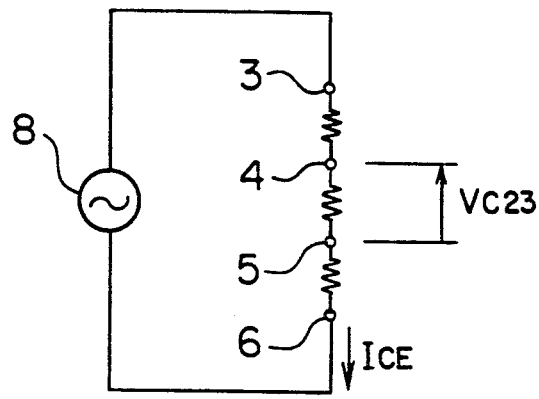
FIG. 3A is an idealized equivalent circuit of the measuring cell used in an electrical conductivity measuring apparatus.
Figure 3B:
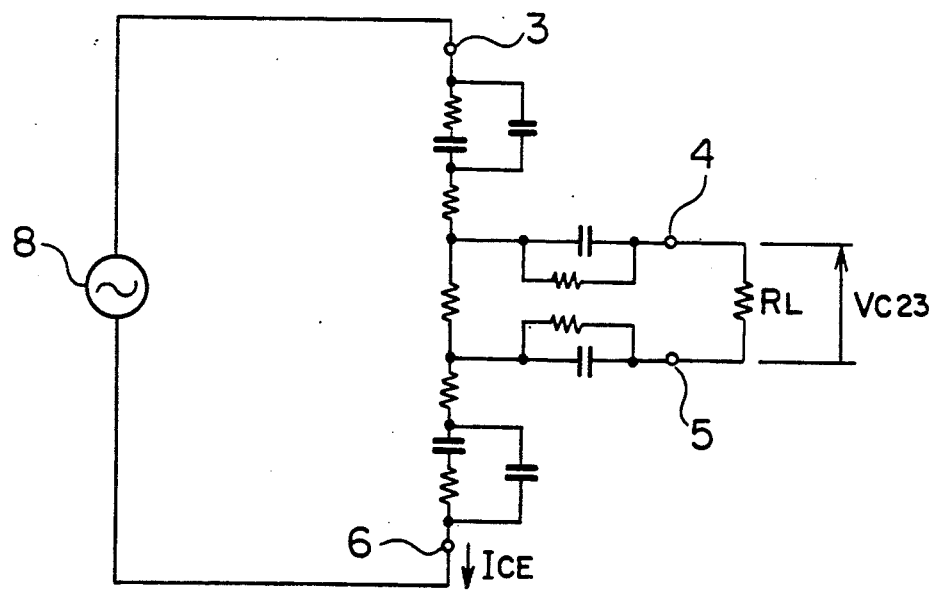
FIG. 3B is a practical equivalent circuit of the measuring cell.

The conventional measuring circuit (FIG. 2) operates correctly only in the case where the cell is represented by a pure resistor model as shown by the equivalent circuit of FIG. 3A. In a practical measuring cell, in which electric double layers and polarization create electrostatic capacity around the electrodes, the cell forms a composite circuit including resistors and electrostatic capacitances as shown in FIG. 3B. The values of electrostatic capacity depend on the concentration and type of electrolyte.

Figure 4:
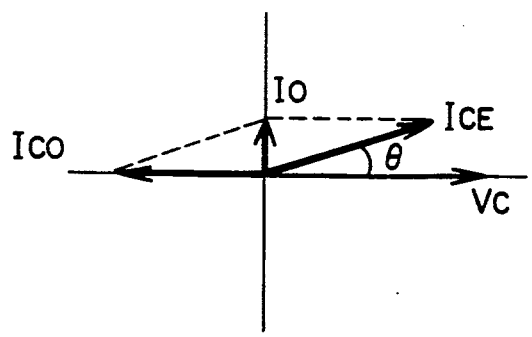
FIG. 4 is a vectorial diagram useful to explain the background compensation by the conventional electrical conductivity measuring apparatus.
Figure 5:
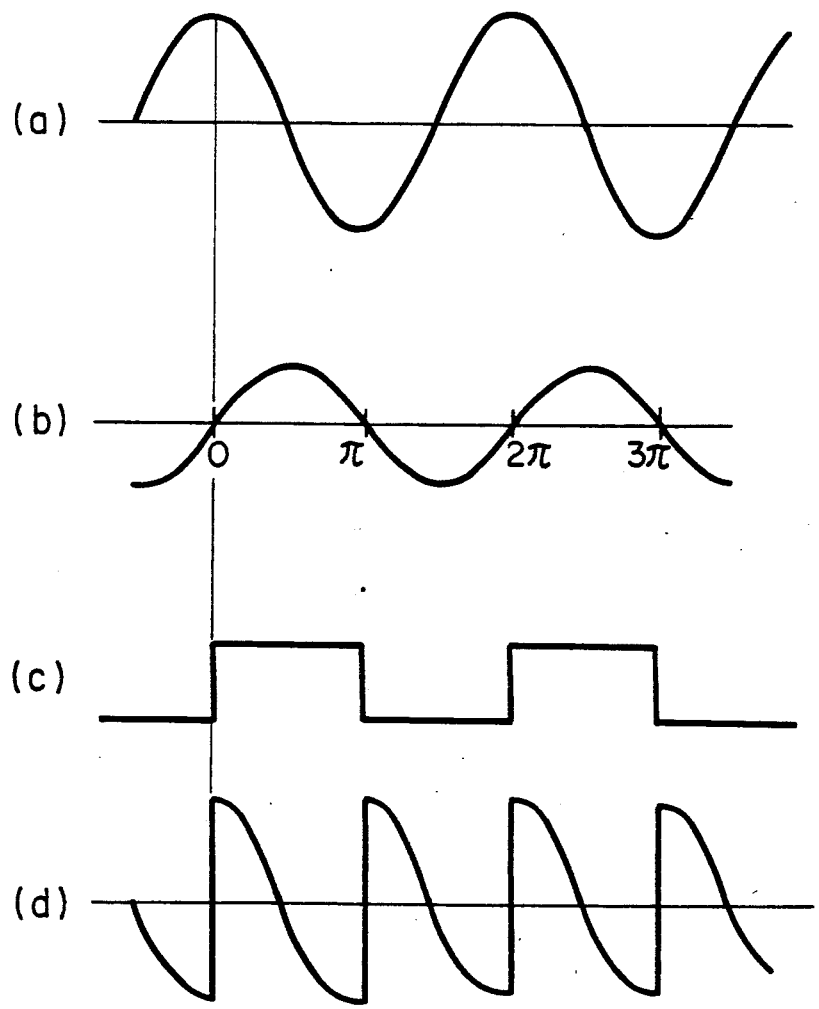
FIGS. 5a–5d are signal waveform diagrams explaining the relation between the phase adjustment and the amplitude of various signals generated in the conventional electrical conductivity measuring apparatus.

FIG. 4 shows the measuring operation based on the conventional background compensation stated above. In the figure, $I_{CE}$ is the current flowing in the measuring cell, and it has a phase shift of $\theta$ relative to the cell application voltage. $I_{CO}$ is the background compensation current, which is derived from the cell application voltage $V_C$ and is different in phase by $\sigma$ (180°) from it. When the amplitude of ICO is increased porgressively, the vector summation, i.e., the output $I_O$ after background compensation has its phase angle rotated from $\theta$ toward $I_{CO}$. At a point of rotation of $$\frac{\pi}{2} \text{ or } -\frac{\pi}{2},$$

the output signal $I_O$ is converted into a voltage and thereafter rendered the synchronous rectification, with the resulting waveform being shown by (d) in FIG. 5.

FIG. 5 shows a set of waveforms at various portions of the circuit shown in FIG. 2. In the figure, indicated by (a) is the waveform of the voltage converted from $I_O$, (b) is the waveform of the cell application voltage $V_C(\omega)$, and (c) is the waveform of the gate signal of synchronous rectification, in which the synchronous rectification circuit is controlled so that the phase of rectification alternates at phase angles $n\pi$ (n=0, 1, 2, ...) of the cell application voltage. FIG. 5 at (d) reveals that when synchronous rectification is conducted for $I_O$ with its phase after background compensation being shifted by $$\frac{\pi}{2} \text{ or } -\frac{\pi}{2}$$

from the phase of synchronous rectification, the output d.c component (i.e., mean value) is nullified, which is the behavior of the conventional background compensation. However, the background compensation current $I_{CO}$ does not have a 180° phase deviation from the cell current, and therefore its a.c. component does not vanish, but remains as shown by $I_O$ in FIG. 4 and at (d) of FIG. 5.

In contrast, according to the present invention, a phase shifter 9 is provided in the compensation current generation circuit 13 in FIG. 1 so that the compensation current and cell current have a 180° phase difference.

Figure 6:
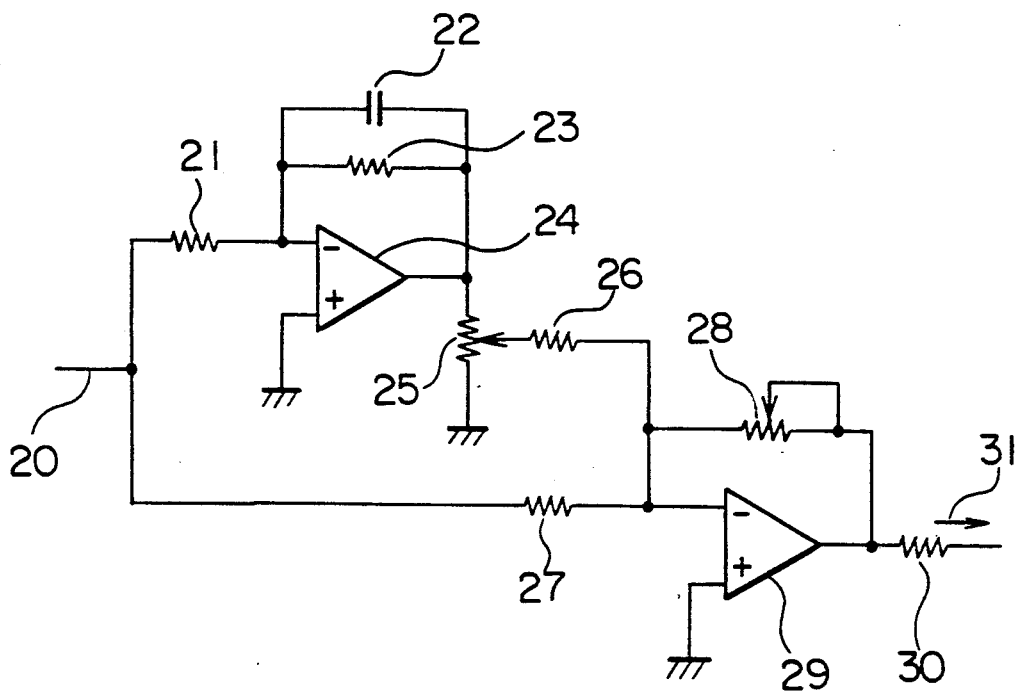
FIG. 6 is a detailed schematic diagram of an example of the compensation current generation circuit indicated by 13 in FIG. 1.

FIG. 6 shows a specific example of the compensation current generation circuit 13 in FIG. 1. In the figure, indicated by 20 is the cell application voltage produced by the differential amplifier 7 in FIG. 1, 21 is a resistor, 22 is a capacitor, 23 is a resistor, 24 is an operational amplifier, 25 is a potentiometer, 26 and 27 are resistors, 28 is a variable resistor, 29 is an operational amplifier, 30 is a resistor, and 31 is the compensation current.

The operational amplifier 24 forms a low-pass filter having a corner frequency set to the frequency of the cell application voltage, which is preferably 1 kHz. The corner frequency on the Bode diagram is known to have its phase angle shifted by $\frac{3}{4}\pi$ (135°), and accordingly the output of the operational amplifier 24 leads the cell application voltage by 135°. The operational amplifier 29 sums the output of the low-pass filter and the input signal on its inverting input terminal. The potentiometer 25 is used to vary the mixing ratio in summing the above-mentioned signals.

The operational amplifier 29 which sums two signals of different phases operates as a vector adder, and it produces an arbitrary signal with a phase range of 0 to $\frac{3}{4}\pi$ depending on the mixing ratio. The phase angle is adjusted so that the current as a result of mixing is coincident in phase with the cell current. Because of the inverting amplifier 29, the compensation current $I_{CO}$ has a phase difference of $\pi$ (180°) from the cell current $I_{CE}$.

Figure 7:
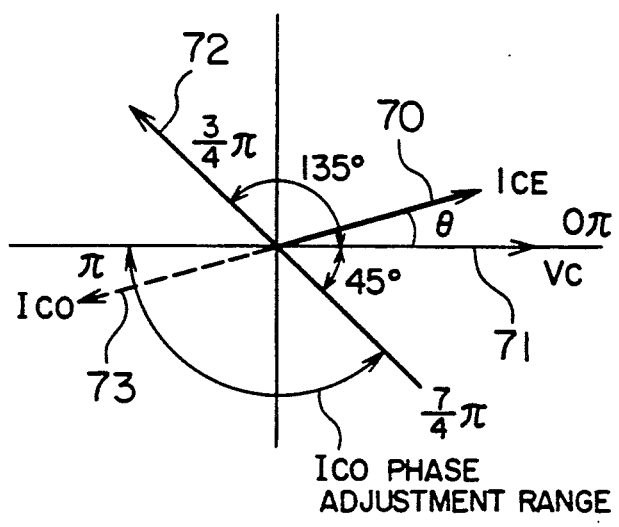
FIG. 7 is a diagram useful to explain the operation of the compensation current generation circuit shown in FIG. 6.

FIG. 7 is a vectorial diagram showing the relation of the foregoing currents. The cell current 70 is out of phase by $\theta$ with the cell application voltage $V_C$ 71. The low-pass filter output 72 is out of phase by $\frac{3}{4}\pi$ (135°) with the cell application voltage. The phase adjustment range of $I_{CO}$ 73 is from $\pi$ to $7/4\pi$.

Returning to FIG. 6, the variable resistor 28 is adjusted so that the cell current $I_{CE}$ and compensation current $I_{CO}$ is equal in amplitude and the $I_{CO}$ and $I_{CE}$ are summed, and both of the a.c. component and d.c. component can be nullified.

Figure 8:
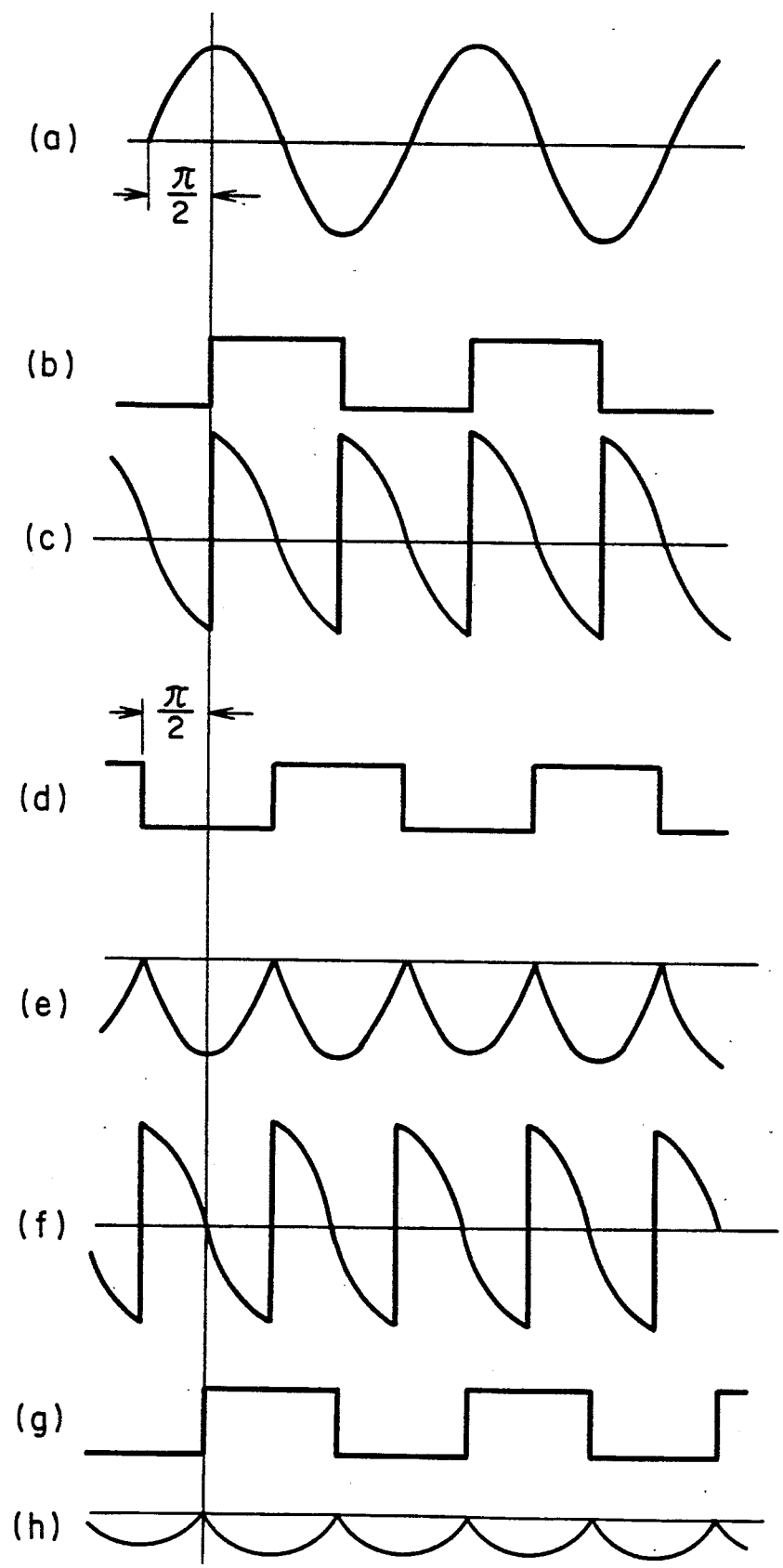
FIGS. 8a-8h are signal waveform diagrams explaining the relation between the phase adjustment and the amplitude of various signals generated in the electrical conductivity measuring apparatus shown in FIG. 1.

More specifically, in FIG. 8 which shows the relation of phase adjustment and the amplitude of various signals produced in various parts of the electrical conductivity measuring apparatus, the amplitude of the compensation current is adjusted first in the conventional manner so that the d.c. component is nullified as shown by (c) in FIG. 8 by following the following procedure.

Initially, the potentiometer 25 is adjusted so that the output current of the low-pass filter 24 flowing into the resistor 26 is brought to zero. Further, the synchronous rectification gate signal generator 17 is set up so that synchronous rectification alternates its phase at phase angles of $n\pi$ (n=0, 1, 2, ...) of cell application voltage. The synchronous rectification gate signal generator 17 will be explained later. With this condition, the variable resistor 28 is adjusted thereby to adjust the amplitude of compensation current, so that the mean value of the output signal of the synchronous rectification circuit whose input is provided by voltage conversion from $I_O$, which is the result of summation of the cell current and compensation current, is nullified. The resulting relation among $I_O$ (shown by (a) in FIG. 8), the phase of synchronous rectification (gate signal of synchronous rectification circuit shown by (b) in FIG. 8), and the synchronous rectification output provided by voltage conversion from $I_O$ (shown by (c) in FIG. 8) is as shown in FIG. 8. Namely, the phase of $I_O$ when the synchronous rectification output becomes zero is shifted by $$\frac{\pi}{2}$$

relative to the phase of cell application voltage (i.e., phase of synchronous rectification). In this manner similar to the conventional method, a coarse adjustment for the compensation current is conducted in advance. Next, the phase of synchronous rectification is shifted by $$\frac{\pi}{2} \ (90°).$$

FIG. 8 shows by (d) the gate signal of the synchronous rectification circuit which produces the output as shown by (e) in FIG. 8. At this stage, the potentiometer 25 in FIG. 6 is adjusted so that the synchronous rectification output has its d.c. component nullified (as shown for its waveform by (f) in FIG. 8). These operations cause $I_O$ to advance its phase by $\pi$ (180°) relative to the cell application voltage, and consequently the compensation current $I_{CO}$ has a phase shift of about 180° from the cell current.

Next, the phase of synchronous rectification is restored to $0\pi$ (0°), and the variable resistor 28 in FIG. 6 is adjusted so that the synchronous rectification output is nullified or minimized. FIG. 8 shows by (g) and (h) the gate signal and rectification output in this state.

By repeating the phase adjustment (FIG. 8 (d), (e), (f)) and compensation current adjustment (FIG. 8 (g), (h)), it is possible to bring the compensation current equal in magnitude to the cell current, and shift the phase by $\pi$ (180°) from the compensation current. Consequently, the summed current $I_O$ can be nullified in both d.c. and a.c. modes.

Figure 9:
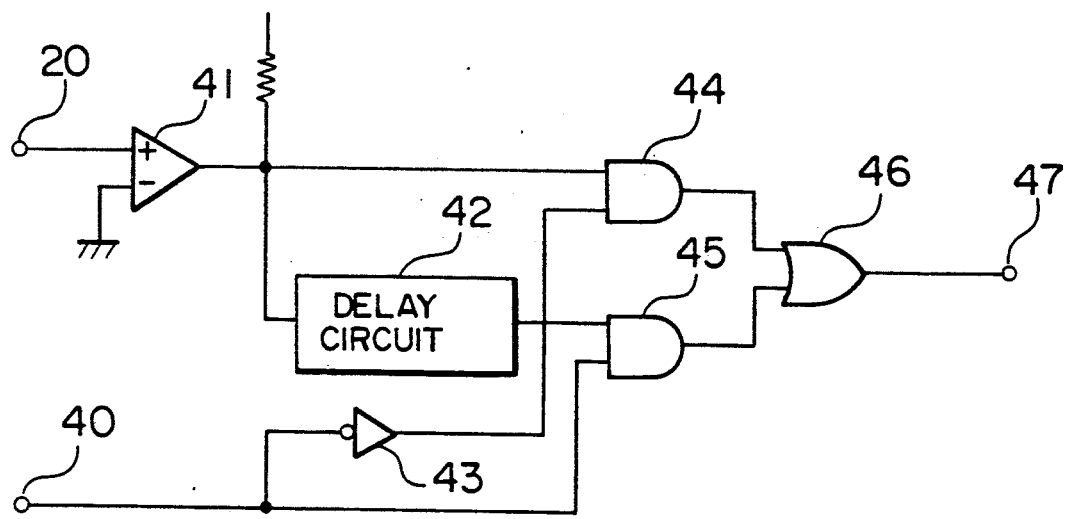
FIG. 9 is a schematic diagram showing a specific example of the synchronous rectification gate signal generator shown in FIG. 1.
Figure 10:
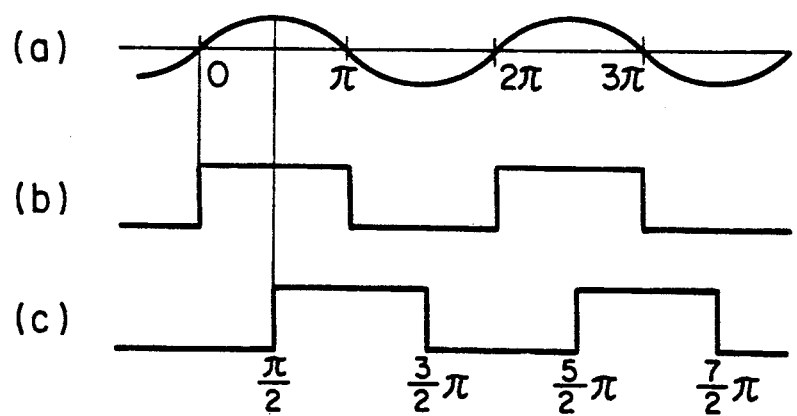
FIGS. 10a-10c are diagrams useful to explain the operation of the circuit shown in FIG. 9.

FIG. 9 shows a specific circuit arrangement of the synchronous rectification gate signal generator, and FIG. 10 shows the waveforms of the input and output signals of the circuit shown in FIG. 9.

In FIG. 9, indicated by 41 is a comparator having a non-inverting input terminal which receives the cell application voltage 20 and an inverting input terminal which has the ground voltage. Indicated by 42 is a delay circuit having a delay time corresponding to the phase angle of $\pi/2$ (0.25 ms when 1 kHz), and it is connected to the output of the comparator 41. An inverter 43 has its input terminal connected to receive the gate switching signal. An AND gate 44 receives the outputs of the comparator 41 and inverter 43. An AND gate 45 receives the outputs of the delay circuit 42 and the gate switching signal. An OR gate 46 which receives the outputs of the AND gates 44 and 45, and produces the synchronous rectification gate signal 47 on its output terminal.

The operation of the synchronous rectification gate signal generator 17 will be explained with reference to FIGS. 9 and 10. By receiving the cell application voltage 20 (shown by (a) in FIG. 10), the comparator 41 produces a "1" output in the positive half cycle of the application voltage and a "0" output in the negative half cycle. When the gate switching signal is "0", the AND gate 44 is selected and a synchronous rectification gate signal of "1" is produced on the output of the OR gate 46 during a period when the cell application voltage has a phase from $2n\pi$ to $(2n+1)\pi (n=0, 1, 2, ...)$, as shown by (b) in FIG. 10. With this gate signal being applied, the synchronous rectification circuit operates for rectification in in-phase with the cell application voltage. On the other hand, when the gate switching signal is "1", the AND gate 45 is selected, and a gate signal 43 of "1" is produced during a period when the output of the delay circuit 42, which delays the output of the comparator 41 by $$\frac{\pi}{2} (90°),$$

is "1", as shown by (c) in FIG. 10. Accordingly, a synchronous rectification gate signal of "1" is produced during a period when the cell application voltage has a phase from $$\frac{\pi}{2} + 2n\pi \text{ to } \frac{\pi}{2} + (2n+1)\pi (n = 0, 1, 2, ...),$$

as shown by (c) in FIG. 10.

By application of one of these gate signals, the synchronous rectification circuit alternates the phase of rectification in synchronism with the gate signal. For example, with a gate signal 40 of "0", the rectification phase is switched at phase angles of $n\pi$ ($n=0, 1, 2, ...$), and the rectification circuit delivers its crude input signal for a phase from 0 to $2\pi$ and delivers its input signal in opposite polarity for a phase from $\pi$ to $2\pi$. With a gate signal 40 of "1", the rectification phase is switched at phase angles of $$\frac{\pi}{2} + n\pi (n = 0, 1, 2, ...),$$

and the rectification circuit delivers its crude input signal for a phase from $$\frac{\pi}{2} \text{ to } \frac{3}{2} \pi$$

and delivers its input signal in opposite polarity for a phase from $$\frac{3}{2} \pi \text{ to } \frac{5}{2} \pi.$$

Although in the embodiment of FIG. 6 the resistor connected between the non-inverting input and output terminals of the operational amplifier 29 is a variable resistor, and the resistor connected to the output terminal is a fixed resistor, they may be a fixed resistor and a variable resistor, respectively.

Another embodiment of the inventive electrical conductivity measuring apparatus will be described with reference to FIGS. 11 and 12.

The electrical conductivity measuring apparatus according to this invention is suitable for the automation of adjustment. In the embodiment of FIG. 11, the functions of the potentiometer 25 and variable resistor 28 for adjustment in the embodiment of FIG. 6 are achieved by D/A converters with the intention of automatic compensating operation. In this connection, the variable resistor 28 is replaced with a fixed resistor and the fixed resistor 30 is replaced with a D/A converter.

Figure 11:
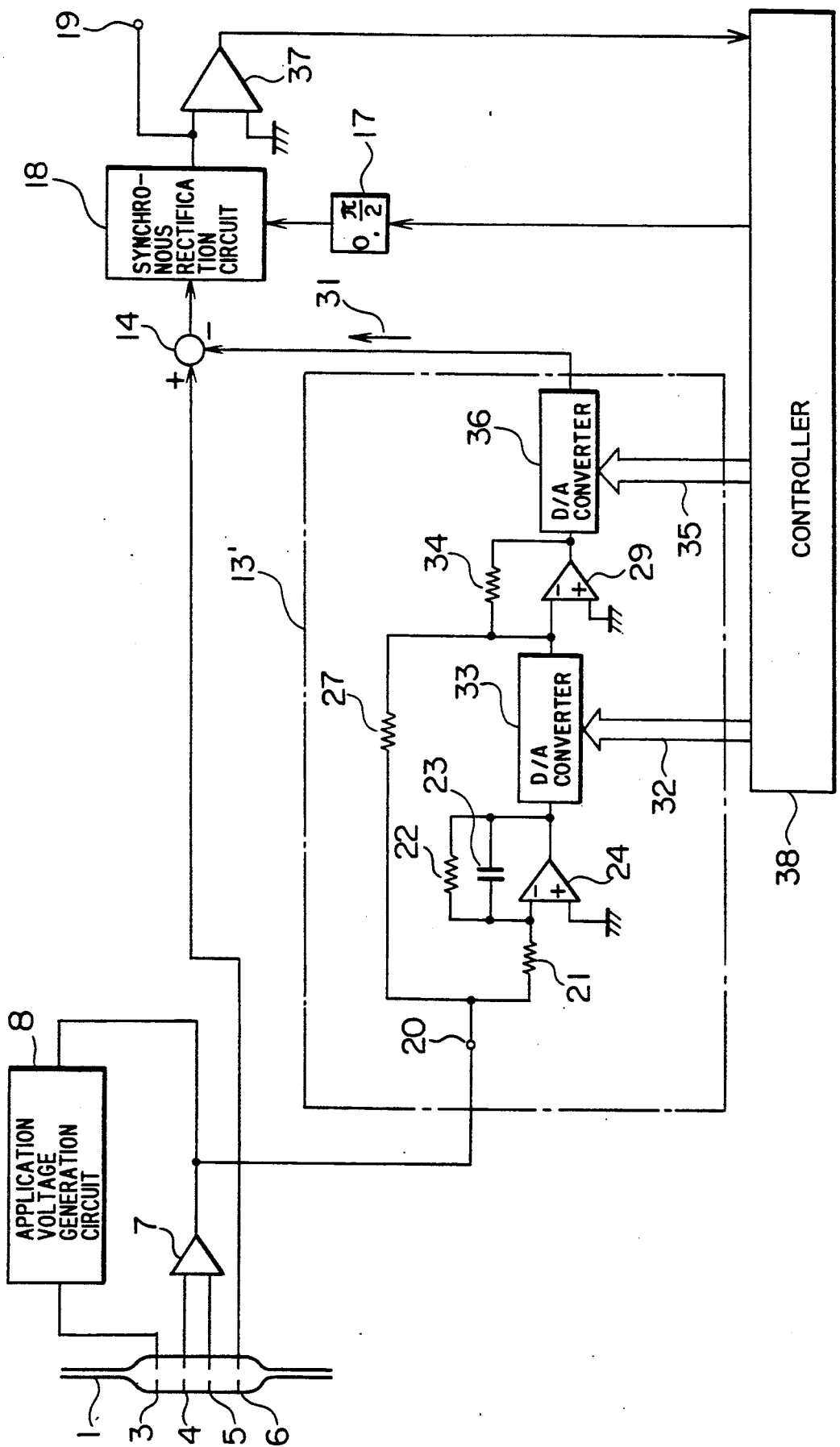
FIG. 11 is a block diagram showing another embodiment of this invention.

In FIG. 11, indicated by 13' is a compensation current generation circuit whose compensation action is automated, and 33 and 36 are D/A converters. Indicated by 37 is a comparator and 38 is a controller which controls the D/A converters 33 and 36 and synchronous rectification gate signal generation circuit 17. Reference numeral 32 denotes phase angle adjustment data and current adjustment data. Other component parts identical to those in FIGS. 1 and 6 are referred to by the same symbols, and their explanation is not repeated.

Figure 12:
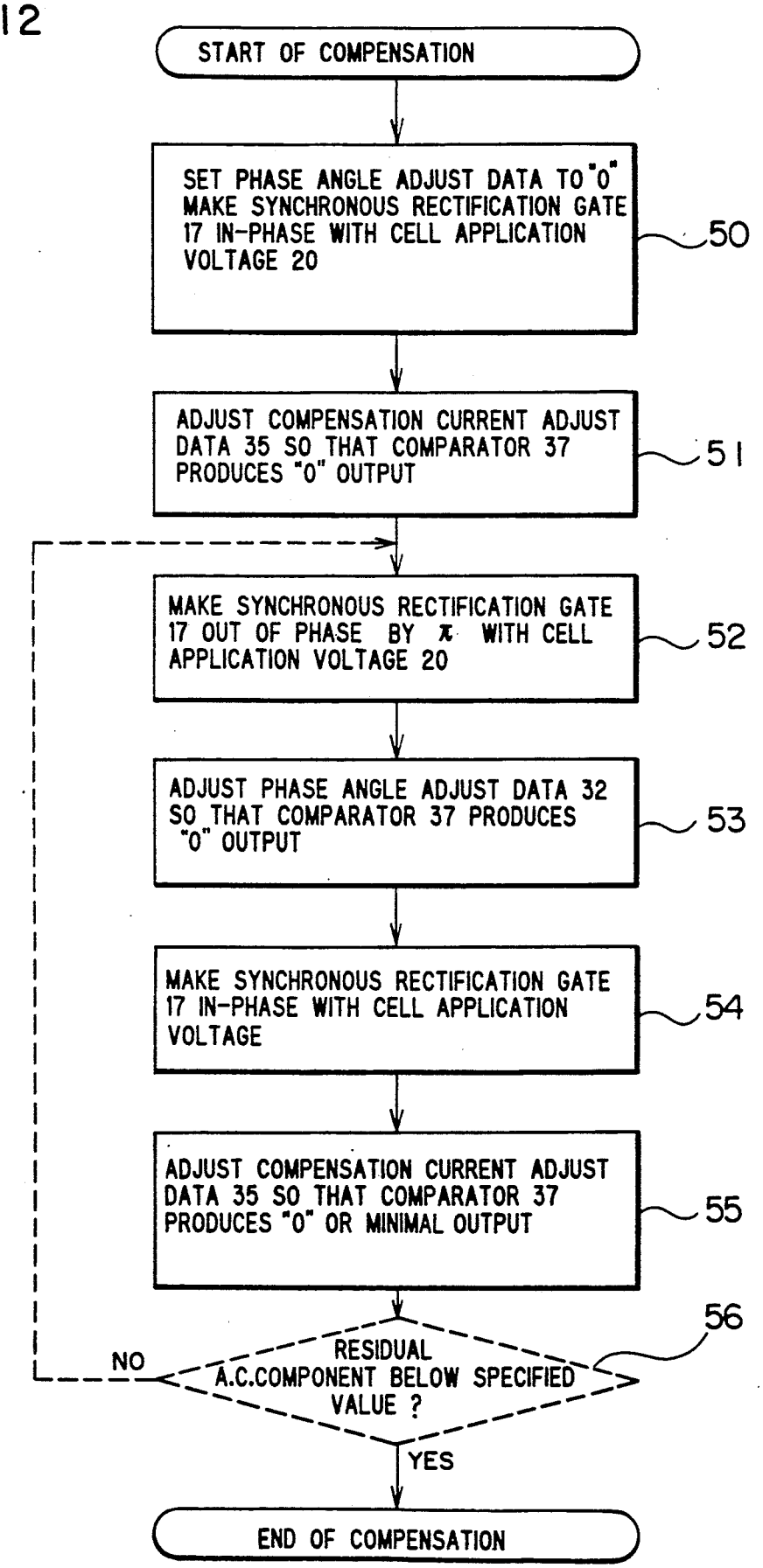
FIG. 12 is a flowchart showing the operation of the controller shown in FIG. 11.

FIG. 12 is a flowchart showing the operation of the controller 38 described in the following. At the commencement of the compensating operation, the controller 38 clears the phase adjustment data 32 to "0", and brings the synchronous rectification gate signal generation circuit 17 in-phase with the cell application voltage 20 (step 50). Next, the controller adjusts the compensation current adjustment data 35 so that the comparator produces a zero output (step 51).

Next, the controller sets the synchronous rectification gate signal generation circuit to have a phase difference of $$\frac{\pi}{2}$$

from the cell application voltage 20 (step 52), and adjusts the phase adjustment data 32 so that the comparator 37 produces a "0" output (step 53). These steps results in a compensation current with a phase difference of about 180° from the cell current.

Next, the controller brings the synchronous rectification gate signal generation circuit 17 in-phase with the cell application voltage (step 54), and adjusts the compensation current adjustment data 35 so that the comparator 37 produces a "0" or minimal output (step 55). These steps result in a compensation current virtually equal in magnitude to the cell current.

Next, the controller judges whether the residual a.c. component has become smaller than the prescribed value (step 56), in which case the compensating operation is completed. Otherwise, the control sequence returns to step 52, and the steps 52-56 are repeated until the compensation current is equal in magnitude to the cell current and differs in phase by $\pi$ (180°) from the cell current.

According to this invention, as described above, in conducting the measurement of electrical conductivity of various electrolytes, a complete background compensation including phase alignment can be made, whereby the operational amplifier is not saturated even at an increased gain for high sensitivity measurement, and accordingly a small change in electrical conductivity of an electrolyte having a large electrical conductivity can be measured. Moreover, because of the operation in the near-zero range of the a.c. component and d.c. component, a phase deviation of synchronous rectification does not turn to noise, and an electrical conductivity measuring apparatus with a high S/N property can be accomplished.

We claim:

1. An apparatus for measuring electrical conductivity, comprising:
   first generation means connected to a measuring cell for generating a predetermined a.c. voltage applied to said cell;
   rectification means connected to said measuring cell for rectifying an a.c. signal flowing through said cell;
   second generation means for producing, based on said a.c. voltage, a compensation current for cancelling a background current flowing through said cell, said compensation current being out of phase by $\pi$ (180°) with said a.c. voltage;
   summing means connected between said measuring cell and said rectification means for summing said background current and said compensation current so as to control said background current; and
   means, included in said second generation means, for correcting the phase of said compensation current in response to a phase derivation of said background current from said a.c. voltage.

2. An electrical conductivity measuring apparatus according to claim 1, wherein said rectification means comprises a synchronous rectification means having means for varying the phase of rectification, said second generation means includes means for varying the values of said compensation current and the amount of phase correction, and wherein the background current cancellation is carried out by adjusting said means for varying the values of said compensation current to set the phase of said synchronous rectification means to reverse at $n\pi$ (n=0, 1, 2 ...) with respect to the phase of said a.c. voltage so that said synchronous rectification means produces a zero or minimal output, and by adjusting the phase compensation value varying means to set the phase of said synchronous rectification means to reverse at $\pi/2+n\pi$ (n=0, 1, 2, ...) with respect to the phase of said a.c. voltage so that said synchronous rectification means produced a zero or minimal output.

3. An electrical conductivity measuring apparatus according to claim 2, wherein said means for varying the values of said compensation current includes a first D/A converter, and said phase compensation value varying means includes a second D/A converter, and wherein said electrical conductivity measuring apparatus further comprises control means for controlling said synchronous rectification phase and said first and second D/A converters.

4. An electrical conductivity measuring apparatus according to claim 1, wherein said second generation means includes a phase shift means for receiving said a.c. voltage and producing a second a.c. signal that is out of phase by a predetermined phase angle with said a.c. voltage; summing means for summing said a.c. voltage and said second a.c. signal in a predetermined proportion to produce said compensation current having a predetermined phase; and means for adjusting the value of said compensation current.

5. An electrical conductivity measuring apparatus according to claim 4, wherein said phase shift means comprises a low-pass filter formed of an operational amplifier.

6. An apparatus for measuring electrical conductivity, comprising:
   at least a pair of electrodes submerged in liquid for receiving a predetermined a.c. voltage to be applied to said liquid;
   first generation means, connected to said electrodes for generating said a.c. voltage applied between said electrodes;
   synchronous rectification means for, in order to evaluate the electrical conductivity of said liquid from the value of an a.c. signal flowing through said electrodes, rectifying said a.c. signal;
   second generation means for producing a compensation current, and means for correcting said compensation current so that said compensation current is equal in magnitude and different in phase by $\pi$(180°) with respect to a background current flowing through said electrodes; and
   summing means, connected between one of said electrodes and said rectification means, for adding said compensation current from said second generation means to said a.c. current from said one electrode so as to cancel to the background electrical conductivity.

7. An electrical conductivity measuring apparatus according to claim 6, wherein said second generation means comprises phase shift means, connected to receive said a.c. voltage, for producing a second a.c. voltage having a phase of said received a.c. voltage shifted to a predetermined phase angle; summing means for summing said a.c. voltage and said second a.c. voltage; and means for adjusting the output of said summing means, said summing means including means for varying the mixing ratio of said a.c. voltage and said second a.c. voltage.

8. An electrical conductivity measuring apparatus according to claim 7, wherein said phase shift means comprises a low-pass filter formed of an operational amplifier.

9. An electrical conductivity measuring apparatus according to claim 7, wherein said synchronous rectification means comprises means for varying the phase of rectification, and wherein said compensation current is adjusted by adjusting the output of summing means to set the phase of said synchronous rectification means to synchronize with phase angles of $n\pi$ (n=0, 1, 2 ...) with respect to the phase of said a.c. voltage so that said synchronous rectification means produces a zero or minimal output, and said mixing ration is adjusted to set the phase of said synchronous rectification means to synchronize with phase angles of $\pi/2+n\pi$ (n=0, 1, 2, ...) with respect to the phase of said a.c. voltage so that said synchronous rectification means produced a zero or minimal output.

10. An apparatus for measuring an electrical conductivity of a substance resolved in solution, comprising:
    a measuring cell containing the solution and receiving a first sinusoidal wave signal with a predetermined magnitude;
    first generation means for generating said first sinusoidal wave signal, a background signal flowing in said cell due to the application of said first sinusoidal wave signal being out of phase from said first sinusoidal wave signal by phase angle which depends on the electrostatic capacity of said solution;
    compensation signal generation means for producing, from said first sinusoidal wave signal, a compensation signal having a predetermined magnitude and predetermined phase; and adjusting means for adjusting said compensation signal so that said compensation signal is equal in magnitude and different in phase by 180° with respect to said background signal; and synchronous rectification means for summing said background signal and said compensation signal and for rectifying the summed signal; wherein the electrical conductivity of said substance is measured from a change in the output of said rectification means between a condition wherein said cell contains only said solution and a condition wherein said cell contains said solution after said substance has been resolved.

11. An electrical conductivity measuring apparatus according to claim 10, wherein said compensation signal generation means comprises:

second generation means for generating a second sinusoidal wave signal that is in-phase with said first sinusoidal wave signal and has a predetermined magnitude;

third generation means for generating a third sinusoidal wave signal, with the phase thereof being shifted by a predetermined phase angle in the same direction as the phase deviation of said background signal with respect to said first sinusoidal wave signal;

means for summing said second sinusoidal wave signal and said third sinusoidal wave signal in a predetermined proportion;

phase reversing means for changing the phase of the summed signal by 180°; and means for adjusting the magnitude of the output of said phase reversing means.

12. An electrical conductivity measuring apparatus according to claim 11, wherein said synchronous rectification means is responsive to a control signal for synchronizing the phase thereof with phase angles of either $n\pi$ or $\pi/2+n\pi$ ($n=0, 1, 2 \ldots$) wherein the phase adjustment for bringing said compensation signal out of phase by with said background signal is carried out by setting the phase of said synchronous rectification means to $\pi/2+n\pi$ and said ratio is adjusted so that the output of said synchronous rectification means is minimized, and the magnitude adjustment for bringing said compensation signal equal in magnitude to said background signal is carried out by setting the phase of said synchronous rectification means to $n\pi$ and the magnitude of the output of said phase reversing means is adjusted by said adjusting means so that the output of said synchronous rectification means is minimized, the phase adjustment and magnitude adjustment being repeated until the output of said synchronous rectification means falls below a predetermined value.

* * * * *